United States Patent
Samejima et al.

(10) Patent No.: US 10,960,205 B2
(45) Date of Patent: Mar. 30, 2021

(54) ELECTRIC TREATMENT DEVICE AND TREATMENT SYSTEM

(71) Applicant: OMRON HEALTHCARE CO., LTD., Muko (JP)

(72) Inventors: Mitsuru Samejima, Kyoto (JP); Yui Watanabe, Kyoto (JP); Makoto Tabata, Kyoto (JP); Tetsuya Sato, Kyoto (JP); Shozo Takamatsu, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 241 days.

(21) Appl. No.: 16/391,350

(22) Filed: Apr. 23, 2019

(65) Prior Publication Data
US 2019/0247646 A1 Aug. 15, 2019

Related U.S. Application Data

(63) Continuation of application No. PCT/JP2017/036102, filed on Oct. 4, 2017.

(30) Foreign Application Priority Data

Nov. 18, 2016 (JP) .............................. JP2016-225218

(51) Int. Cl.
*A61N 1/36* (2006.01)
*A61N 1/08* (2006.01)
(Continued)

(52) U.S. Cl.
CPC .................. *A61N 1/08* (2013.01); *A61B 5/05* (2013.01); *A61B 5/053* (2013.01); *A61N 1/0452* (2013.01);
(Continued)

(58) Field of Classification Search
None
See application file for complete search history.

(56) References Cited

U.S. PATENT DOCUMENTS 9,314,644 B2* 4/2016 Wu .................... A61F 7/007
2004/0111124 A1* 6/2004 Walker ............... A61B 5/7264
607/7

(Continued)

FOREIGN PATENT DOCUMENTS

JP 5-168721 A 7/1993
JP 9-056829 A 3/1997
(Continued)

OTHER PUBLICATIONS

Official Communication issued in International Patent Application No. PCT/JP20171036102, dated Nov. 28, 2017.

*Primary Examiner* — Kennedy Schaetzle
(74) *Attorney, Agent, or Firm* — Keating and Bennett, LLP (57) ABSTRACT

An electric treatment device includes an impedance detector to measure bioelectrical impedance at a site of a body of a user by using electrodes in contact with the site, a voltage controller to perform treatment of the site by controlling a voltage applied to the electrodes, and a timer to set a target time from when treatment of the site is started by the voltage controller to when the voltage value of the applied voltage reaches the target voltage value, based on the measured bioelectrical impedance. The greater the measured bioelectrical impedance is, the shorter the timer sets the target time. The voltage controller increases the voltage value of the applied voltage to the target voltage value based on the set target time.

6 Claims, 7 Drawing Sheets

(51) Int. Cl.
*A61N 1/04* (2006.01)
*A61B 5/053* (2021.01)
*A61B 5/05* (2021.01)
*A61N 1/372* (2006.01)

(52) U.S. Cl.
CPC ............ *A61N 1/0492* (2013.01); *A61N 1/36* (2013.01); *A61N 1/36014* (2013.01); *A61N 1/37247* (2013.01); *A61N 2001/083* (2013.01)

(56) References Cited

U.S. PATENT DOCUMENTS

2017/0021172 A1* 1/2017 Perez .................. A61N 1/36031
2019/0143116 A1* 5/2019 Mowery ............ A61N 1/36031
607/53

FOREIGN PATENT DOCUMENTS

JP 2009-125510 A 6/2009
JP 2012-532672 A 12/2012

\* cited by examiner

FIG. 10

ELECTRIC TREATMENT DEVICE AND TREATMENT SYSTEM

CROSS REFERENCE TO RELATED APPLICATIONS

This application claims the benefit of priority to Japanese Patent Application No. 2016-225218 filed on Nov. 18, 2016 and is a Continuation Application of PCT Application No. PCT/JP2017/036102 filed on Oct. 4, 2017. The entire contents of each application are hereby incorporated herein by reference.

BACKGROUND OF THE INVENTION

1. Field of the Invention

The present disclosure relates to an electric treatment device and a treatment system.

2. Description of the Related Art

Conventionally, an electric treatment device has been known in which multiple pads are adhered to a surface of a body such as an abdomen or a back, and a low-frequency pulse is output to a muscle inside the body via the pad to electrically stimulate the muscle.

For example, JP 2009-125510A discloses a health promotion device that is a low-frequency treatment device with a swelling measurement function. This health promotion device includes: a swelling measurement unit that measures swelling of a part of a body by measuring impedance at a time when a part of the body of a user is placed between two measurement current electrodes and current is applied; and a low-frequency treatment unit that has a low-frequency electrode that applies a low-frequency current for causing muscle contraction.

In the case of using an electric treatment device, usually, the intensity of electric stimulation that feels comfortable is different for each user, and therefore the user needs to start treatment after setting the strength to his or her preference. The setting task is a task that is complicated for a user who often uses the electric treatment device.

Also, how the user feels the electric stimulation depends on the state of the body of the user (e.g., the state in which the skin is moist, the state in which the skin is dry, or the like). For this reason, when a current obtained based on the electric stimulation set by the user is rapidly output at the treatment start time, depending on the state of the body at this time (e.g., the case of being in state in which the skin is moist and electric stimulation is easily felt), there is a likelihood that the user will experience an unpleasant sensation. In order to avoid this, the user needs to perform a complicated task such as gradually increasing the strength of the electric stimulation by manually performing output adjustment.

JP 2009-125510A discloses that swelling of a part of the body at a treatment time at which an attempt is made to perform low-frequency treatment is measured and an optimal low-frequency treatment is performed according to the state of swelling at the treatment time, but JP 2009-125510A discloses no technique for solving the above-described problem.

SUMMARY OF THE DISCLOSURE

Preferred embodiments of the present disclosure provide electric treatment devices and treatment systems each of which makes it possible to perform optimal treatment according to a state of a body of a user without having the user perform a complicated task.

An electric treatment device according to a preferred embodiment of the present invention includes an impedance detector to measure bioelectrical impedance at a site of a body of a user, using a plurality of electrodes in contact with the site; a voltage controller to perform treatment of the site by controlling a voltage applied to the plurality of electrodes; and a timer to set a target time from when treatment of the site is started by the voltage controller to when the voltage value of the applied voltage reaches a target voltage value, based on the measured bioelectrical impedance. The greater the measured bioelectrical impedance is, the shorter the timer sets the target time. The voltage controller increases the voltage value of the applied voltage to the target voltage value based on the set target time.

Preferably, the voltage controller increases the voltage value of the applied voltage such that a second increase rate of the voltage value in a period from a time when the voltage value of the applied voltage reaches a predetermined reference value to when the target voltage value is reached is smaller than a first increase rate of the voltage value in a period from when treatment of the site is started to when the voltage value of the applied voltage reaches the predetermined reference value.

Preferably, the electric treatment device includes a plurality of treatment modes. The target voltage value is determined in advance for each of the plurality of treatment modes. The timer sets the target time based on the measured bioelectrical impedance and the target voltage value corresponding to a treatment mode selected by the user from the plurality of treatment modes.

Preferably, the target voltage value is a voltage value corresponding to an intensity of electric stimulation desired by the user.

Preferably, the electric treatment device is a low-frequency treatment device.

A treatment system according to another preferred embodiment includes a terminal apparatus, and an electric treatment device to be able to perform wireless communication with the terminal apparatus. The electric treatment device includes an impedance detector to measure bioelectrical impedance at a site of a body of a user, using a plurality of electrodes in contact with the site; a voltage controller to perform treatment of the site by controlling a voltage applied to the plurality of electrodes, in accordance with an instruction from the terminal apparatus; and a timer to set a target time from when treatment of the site is started by the voltage controller when the voltage value of the applied voltage reaches a target voltage value, based on the measured bioelectrical impedance. The greater the measured bioelectrical impedance is, the shorter the timer sets the target time. The voltage controller increases the voltage value of the applied voltage to the target voltage value based on the set target time.

According to preferred embodiments of the present invention, improved or optimal treatment is able to be performed according to the state of the body of the user without having the user perform a complicated task.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Hereinafter, preferred embodiments of the present invention will be described with reference to the drawings. In the following description, identical components are denoted by identical reference numerals. The names and functions thereof are also the same. Accordingly, detailed description thereof will not be repeated.

Preferred Embodiment 1

Figure 1:
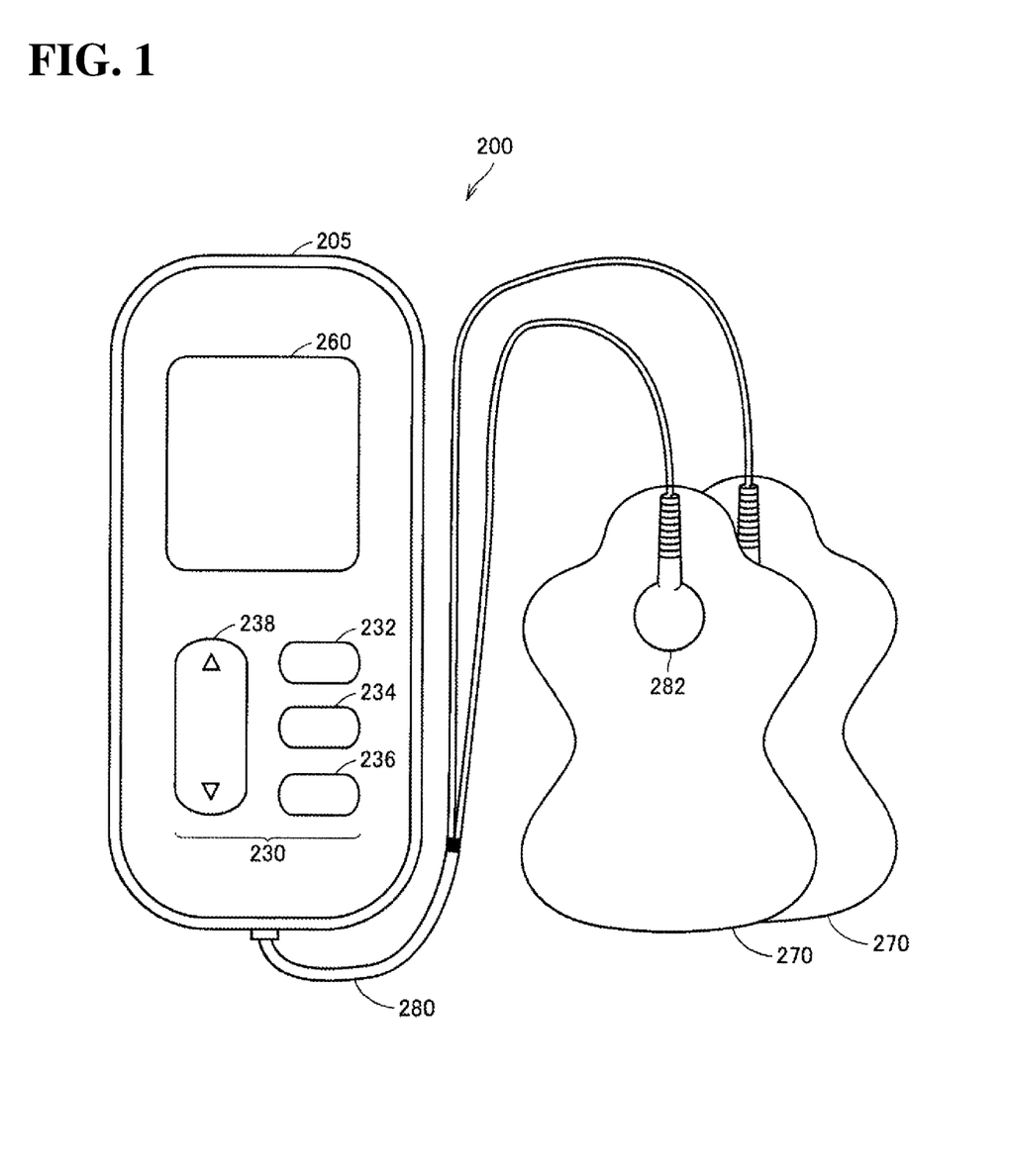
FIG. 1 is a diagram showing an example of an external appearance of an electric treatment device according to Preferred Embodiment 1 of the present invention.

FIG. 1 is a diagram showing an example of an external appearance of an electric treatment device according to Preferred Embodiment 1.

With reference to FIG. 1, an electric treatment device 200 according to Preferred Embodiment 1 mainly includes: a main body 205 of the treatment device; a pair of pads 270 to adhere to a treatment site; and a cord 280 to electrically connect the main body 205 and the pads 270. The electric treatment device 200 is of a wired type, and is a low-frequency treatment device that performs treatment such as easing shoulder stiffness of a user by supplying a low-frequency pulse current. For example, the frequency of the low-frequency pulse current is 1 Hz to 1200 Hz. Note that the electric treatment device 20 may also have a pulse current in a frequency band other than this.

The pads 270 are sheet-shaped and are attached to the body of the user. One surface of the pad 270 (the surface that does not come into contact with the body) is provided with a plug that corresponds to an electrode on the other surface (the surface that comes into contact with the body). The electrode is made of, for example, a conductive gel material, or the like. A plug 282 of the cord 280 and a plug on the pad 270 are connected and the cord 280 is inserted into a jack of the main body 205 to connect the main body 205 and the pad 270. It should be noted that if the polarity of the electrode on one of the pads 270 is positive, the polarity of the electrode on the other pad 270 is negative.

The main body 205 is provided with an operation interface 230 including various buttons, and a display 260. The operation interface 230 includes: a power button 232 to switch the power source on and off; a mode selection button 234 to perform selection of a treatment mode; a treatment start button 236; and an adjustment button 238 to perform adjustment of the intensity of electric stimulation (hereinafter also referred to as "electric stimulation intensity"). Note that the operation interface 230 is not limited to the above-described configuration and need only be a configuration that can realize various operations performed by a later-described user. The operation interface 230 may also include, for example, other buttons, a dial, a switch, or the like.

The display 260 displays the electric stimulation intensity, remaining treatment time, the treatment mode, the attachment state of the pad 270, and the like, and displays various messages.

Figure 2:
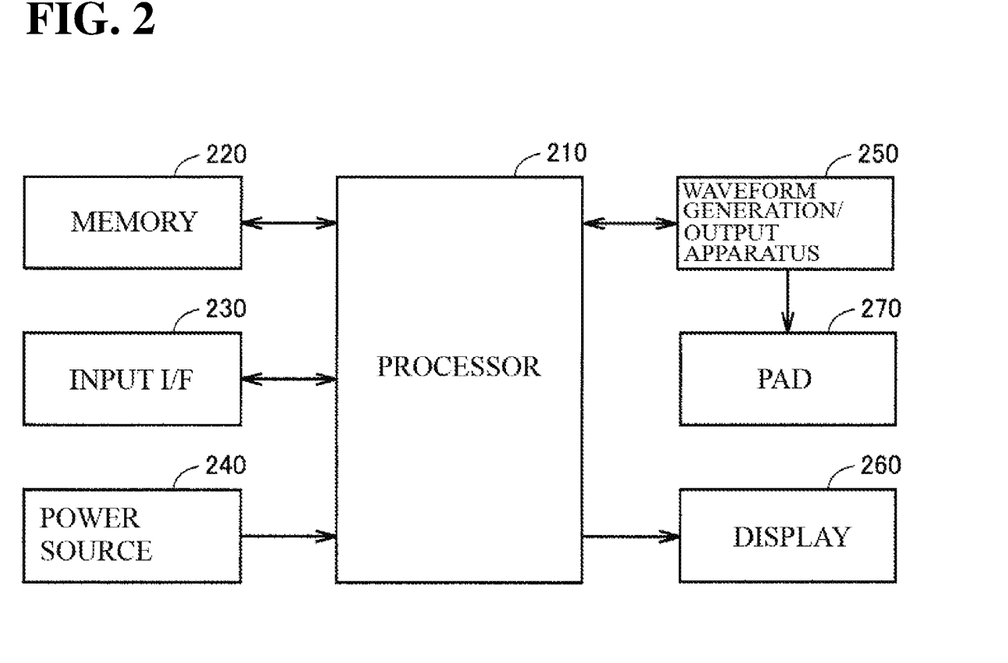
FIG. 2 is a block diagram showing an example of a hardware configuration of an electric treatment device according to Preferred Embodiment 1 of the present invention.

FIG. 2 is a block diagram showing an example of a hardware configuration of an electric treatment device 200 according to Preferred Embodiment 1. With reference to FIG. 2, the electric treatment device 200 includes a processor 210, a memory 220, an operation interface 230, a power source 240; a waveform generation/output apparatus 250; and a display 260.

The processor 210 is typically an arithmetic processing unit such as a CPU (central processing unit) or an MPU (multi-processing unit). The processor 210 is configured or programed to function as a controller to control operations of the units of the electric treatment device 200 by reading out and executing a program stored in the memory 220. The processor 210 realizes each process (step) of the later-described electric treatment device 200 by executing the program.

The memory 220 is realized by a RAM (random access memory), a ROM (read-only memory), a flash memory, or the like. The memory 220 stores a program to be executed by the processor 210, data to be used by the processor 210, or the like.

The operation interface 230 receives input of an operation on the electric treatment device 200 and may include various buttons such as those described above. When various buttons are operated by the user, signals resulting from the operation are input to the processor 210.

The power source 240 supplies electric power to the elements of the electric treatment device 200. For example, an alkaline battery is used as the power source, and the power source 240 stabilizes the battery voltage and generates a drive voltage to be supplied to the elements.

The waveform generation/output apparatus 250 outputs a current (hereinafter also referred to as "treatment current") that is to flow in the treatment site of the body of the user via the pads 270. The waveform generation/output apparatus 250 includes a booster circuit, a voltage adjustment circuit, an output circuit, a current detection circuit, and the like.

The booster circuit boosts the power source voltage to a predetermined voltage. The voltage adjustment circuit adjusts the voltage that was boosted by the booster circuit to a voltage corresponding to the electric stimulation intensity set by the user. Specifically, with the electric treatment device 200, the adjustment of the electric stimulation can be set to a predetermined number of stages (e.g., 10 stages) using the adjustment button 238. The processor 210 receives input of a setting of the electric stimulation intensity via the adjustment button 238 and instructs the waveform generation/output apparatus 250 (voltage adjustment circuit) to perform adjustment to a voltage corresponding to the received electric stimulation intensity.

The output circuit generates a treatment waveform (pulse waveform) corresponding to the treatment mode based on the voltage adjusted by the voltage adjustment circuit and outputs the treatment waveform to the pads 270 (the electrodes thereof) via the cord 280. Specifically, when an operation such as switching the treatment mode or changing the electric stimulation intensity is performed by the user via the operation interface 230, a control signal corresponding to the content of the operation is input to the output circuit from the processor 210. The output circuit outputs a treatment waveform according to the control signal.

In view of this, multiple treatment modes are prepared in advance in the electric treatment device 200. Examples of treatment modes include "massage", "tap", and "press" modes.

The output circuit can change the electric stimulation corresponding to the various modes such as "massage", "tap", and "press" by changing the waveform of the pulse (includes the pulse width, pulse interval, and output polarity). Also, the electric stimulation intensity can be adjusted by changing the amplitude of the pulse. Known waveforms can be used as the specific treatment waveforms. It should be noted that the treatment waveform may also be an alternating current waveform instead of a pulse waveform.

The current detection circuit detects the value of a current that flows between the pair of pads 270 and outputs a signal indicating the detected value to the processor 210. Specifically, the processor 210 instructs the waveform generation/output apparatus 250 (waveform adjustment circuit) to apply a minute voltage between the pair of pads 270 in order to apply a minute current for bioelectrical impedance measurement to the treatment site of the body of the user. The voltage adjustment circuit applies the minute voltage in accordance with the instruction given by the processor 210. The processor 210 calculates (measures) the bioelectrical impedance of the treatment site based on the value of the current that flowed between the pair of pads 270 via the treatment site and the value of the minute voltage, which were input from the current detection circuit. It should be noted that the minute current is a current that does not stimulate the body of the user (e.g., the current value is 2 mA or less).

Also, the processor 210 can use the current value input from the current detection circuit to detect whether the pads 270 are attached (adhered) to the user or the pads 270 are not attached to (are off of) the user. Specifically, if the current value is a predetermined value or more, the processor 210 determines that the pads 270 are attached to the user, and if the current value is less than a predetermined value, the processor 210 determines that the pads 270 are not attached to the user. This makes use of the principle that if at least one of the pair of pads 270 is not suitably attached to the user, a current loop in which current is output from one of the pads 270, passes through the body, and returns to the other pad 270 is not established, and therefore current of a predetermined value or more does not flow.

For example, the display 260 preferably is an LCD (liquid crystal display) and displays various types of information according to instructions from the processor 210.

Next, the way in which the electric treatment device 200 according to Preferred Embodiment 1 provides electric stimulation to the user will be described.

As described above, for a user who frequently receives treatment, the task of setting the user's preferred electric stimulation intensity each time is a task that is troublesome. Also, depending on the state of the body of the user, if a current obtained based on a set electric stimulation intensity is rapidly output, there is a likelihood that the user will be given an unpleasant sensation.

In view of this, the electric treatment device 200 according to Preferred Embodiment 1 registers (stores) the current value corresponding to the user's preferred electric stimulation intensity (hereinafter also referred to as "desirable stimulation intensity") in the memory 220 in advance. Then, the electric stimulation device 200 adjusts the time until the registered desirable stimulation intensity is reached, according to the bioelectrical impedance of the treatment site of the user at the start of treatment.

Figure 3:
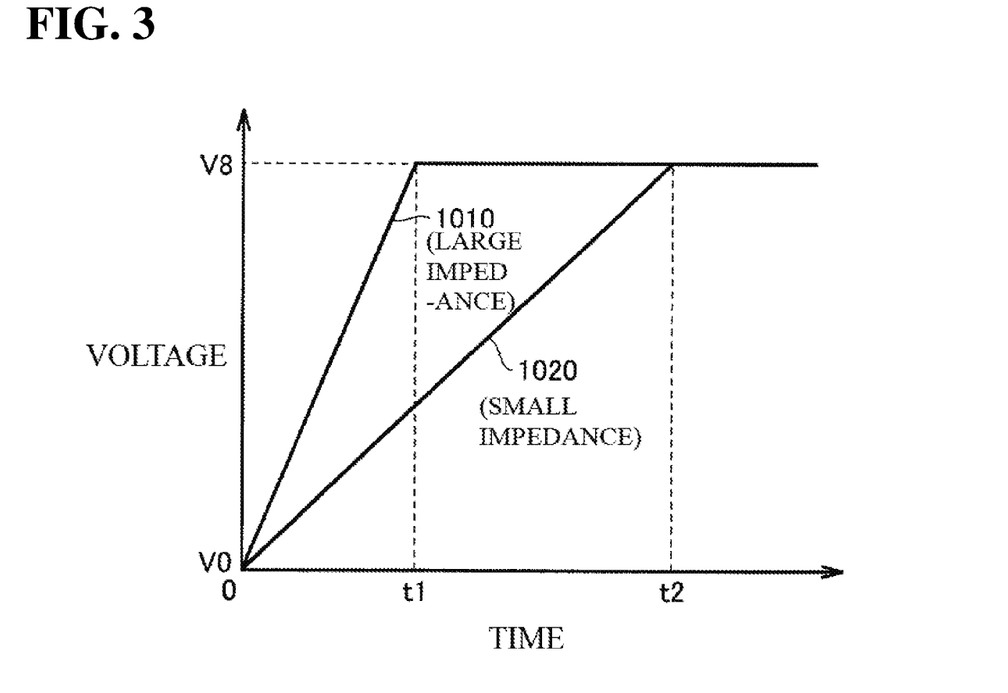
FIG. 3 is a diagram showing an example of a way in which electric stimulation is provided by an electric treatment device according to Preferred Embodiment 1 of the present invention.

FIG. 3 is a diagram showing an example of a way in which electric stimulation is provided by the electric treatment device 200 according to Preferred Embodiment 1. Here, a case is envisioned in which the electric stimulation intensity can be set in 10 stages, "9" being the highest intensity and "0" being the lowest intensity. Also, the desirable stimulation intensity is registered as "8", and this is set as the target intensity. Note that the voltage values corresponding to the electric stimulation intensities "0" to "9" are expressed as "V0" to "V9" respectively, and it is assumed that the voltage value "V0" is 0 V. The horizontal axes of FIGS. 3 and 4 indicate the time, and the vertical axes indicate the voltage value of the voltage applied between the pair of pads 270 from the main body 205 (more specifically, the amplitude value of the applied voltage).

With reference to FIG. 3, the greater the bioelectrical impedance of the treatment site is, the more the electric treatment device 200 shortens the target time until the target voltage V8, which corresponds to the target intensity "8", is reached from the voltage value V0 at the treatment start time. Specifically, if the bioelectrical impedance is great, the target time is set to be short (here, set to t1), and therefore the voltage value increases rapidly as in graph 1010. On the other hand, if the bioelectrical impedance is small, the target time is set to be long (here, set to t2), and therefore the voltage value increases slowly as in graph 1020.

Typically, the electric treatment device 200 stores the bioelectrical impedance and the average rate of increasing the voltage value in association with each other in the memory 220. The electric treatment device 200 references the memory 220 to set the target time for reaching the target intensity. For example, if the bioelectrical impedance is Z1, the average rate is associated with S1, and if the bioelectrical impedance is Z2 (>Z1), the average rate is associated with S2 (=2S1). In this case, the target time corresponding to the bioelectrical impedance Z2 is set to half of the length compared to the target time corresponding to the bioelectrical impedance Z1.

Accordingly, if the user's skin is moist and electric stimulation is easily felt (bioelectrical impedance is small), the electric stimulation intensity increases relatively slowly, and therefore an unpleasant sensation is not given to the user. On the other hand, if the user's skin is dry and electric stimulation is not easily felt (bioelectrical impedance is great), the electric stimulation intensity increases relatively rapidly, and therefore the user's desired electric stimulation intensity can be reached quickly. In this manner, the user can receive comfortable electric stimulation suitable for the state of the body of the user without performing a troublesome task.

Figure 4:
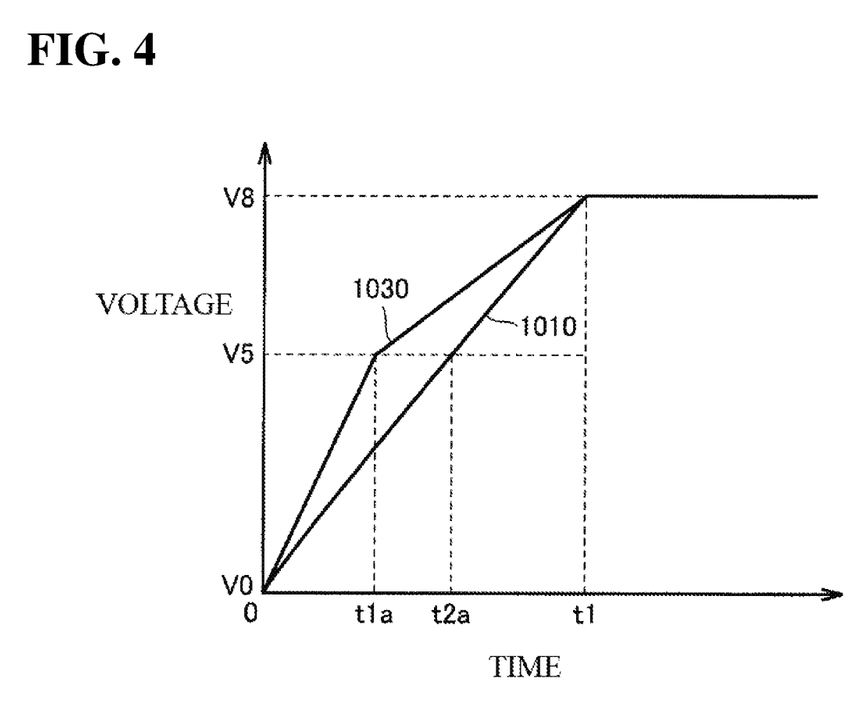
FIG. 4 is a diagram showing another example of a way in which electric stimulation is provided by the electric treatment device according to Preferred Embodiment 1 of the present invention.

In the example shown in FIG. 3, an example was described in which the voltage value is increased at a certain rate in a period from the treatment start time to when the target voltage is reached, but there is no limitation to this configuration. For example, as in the example shown in FIG. 4, it is also possible to use a configuration in which the rate in the period from the treatment start time to when the target voltage is reached is changed. FIG. 4 is a diagram showing another example of the way in which electric stimulation is provided by the electric treatment device 200 according to Preferred Embodiment 1.

With reference to FIG. 4, in graph 1010, the time from the treatment start time to when the applied voltage reaches the voltage value V5 is t2a, whereas in graph 1030, the time is t1a (<t2a). On the other hand, in both graph 1010 and graph 1030, the overall time from the treatment start time to when the applied voltage reaches the target voltage value V8 is t1, which is the same. As shown in graph 1030, the electric treatment device 200 may also perform control such that the increase rate (rate at which the voltage value increases) Sb in the period from when the voltage value V5 is reached to when the target voltage value V8 is reached is lower than the increase rate Sa in the period from the treatment start time to when the applied voltage reaches a predetermined reference value (here, the voltage value V5).

Accordingly, in the period immediately after the start of treatment in which the electric stimulation intensity applied to the user is small (i.e., the voltage value is less than the reference value), the electric stimulation intensity increases relatively rapidly, and if the electric stimulation intensity applied to the user becomes large (i.e., if the voltage value becomes greater than or equal to the reference value), the electric stimulation intensity increases relatively slowly in order to allow the user to gradually acclimate to the strong electric stimulation. For this reason, it is possible to further reduce the likelihood that the user will be given an unpleasant sensation. Also, the time t1 until the desirable stimulation intensity is reached is the same in the example shown in FIG. 3 and the example shown in FIG. 4.

In FIGS. 3 and 4, a case was described in which the user's desirable stimulation intensity is "8". The electric treatment device 200 has multiple treatment modes (e.g., three modes, namely "massage", "tap", and "press"). Here, even if set to the same electric stimulation intensity, the electric stimulation will feel different to the user depending on the treatment mode. For this reason, the electric treatment device 200 may also register the desirable stimulation intensity (or the voltage value corresponding to the desirable stimulation intensity) in the memory 220 in advance for each of the multiple treatment modes. In this case, the electric treatment device 200 sets the desirable stimulation intensity corresponding to a treatment mode selected by the user from the multiple treatment modes as the target intensity.

As an example of a registration method, a method is conceivable in which the user experiences electric stimulation in each treatment mode, the user selects his or her preferred electric stimulation intensity for each of the multiple treatment modes, and the selected electric stimulation intensities are registered.

Figure 5:
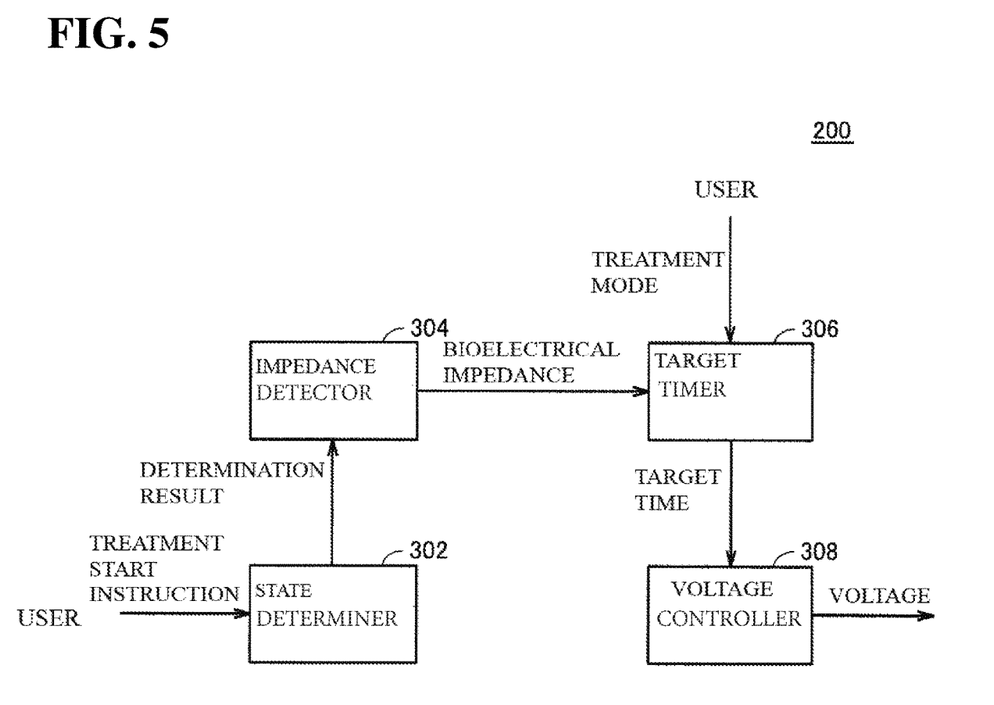
FIG. 5 is a block diagram showing a functional configuration of an electric treatment device according to Preferred Embodiment 1 of the present invention.

FIG. 5 is a block diagram showing a functional configuration of the electric treatment device 200 according to Preferred Embodiment 1. Referring to FIG. 5, the electric treatment device 200 includes a state determiner 302, an impedance detector 304, a target timer 306, and a voltage controller 308.

The state determiner 302 determines whether or not the multiple electrodes are in contact with the user based on the value of the current that flows between the multiple electrodes (between the electrodes of the pair of pads 270) in contact with the treatment site of the body of the user. Specifically, if the current value is a predetermined value or more, the state determiner 302 determines that the multiple electrodes are in contact (i.e., that the pair of pads 270 are attached to the user), and if the current value is less than a predetermined value, the state determiner 302 determines that at least one of the multiple electrodes is not in contact (i.e., that at least one of the pair of pads 270 is not attached to the user). In a certain aspect, the state determiner 302 performs the determination if a treatment start instruction is received from the user via the operation interface 230. Typically, the state determiner 302 is realized by the processor 210 and the waveform generation/output apparatus 250.

The impedance detector 304 measures the bioelectrical impedance of the treatment site using multiple electrodes in contact with the treatment site of the body of the user. Specifically, if the pair of pads 270 are attached to the user, the impedance detector 304 measures the bioelectrical impedance of the treatment site based on the value of the current that flowed between the pair of pads 270 via the treatment site, and the value of the voltage applied between the pair of pads 270.

In a certain aspect, the impedance detector 304 measures the bioelectrical impedance at a time after the treatment start instruction has been provided by the user and before the treatment of the treatment site is started by the voltage controller 308. Also, in another aspect, the impedance detector 304 may also measure the bioelectrical impedance when an instruction to start the impedance measurement is received from the user via the operation interface 230. Typically, the impedance detector 304 is realized by the processor 210 and the waveform generation/output apparatus 250.

The voltage controller 308 performs treatment of the treatment site by controlling the voltage applied between the pair of pads 270 according to the instruction provided by the user via the operation interface 230.

Based on the bioelectrical impedance measured by the impedance detector 304, the target timer 306 sets the target time from when treatment of the treatment site is started by the voltage controller 308 to when the voltage value of the applied voltage reaches the target voltage (i.e., the voltage value corresponding to the desirable stimulation intensity). Specifically, the greater the measured bioelectrical impedance is, the shorter the target timer 306 sets the target time. Also, if the target voltage value is determined in advance for each of the multiple treatment modes, the target timer 306 sets the target time based on the measured bioelectrical impedance and the target voltage value corresponding to the treatment mode selected by the user from the multiple treatment modes. Typically, the target timer 306 is realized by the processor 210.

The voltage controller 308 increases the voltage value of the applied voltage to the target voltage value based on the target time set by the target timer 306. In a certain aspect, the voltage controller 308 increases the voltage value of the applied voltage such that the increase rate (e.g., increase rate Sb) of the voltage value in the period from the time when the voltage value of the applied voltage reaches the reference value to when the target value is reached is smaller than the increase rate (e.g., increase rate Sa) of the voltage value in the period from when treatment of the treatment site is started to when the voltage value of the applied voltage reaches the reference value (e.g., voltage value V5). Typically, the voltage controller 308 is realized by the processor 210 and the waveform generation/output apparatus 250.

Figure 6:
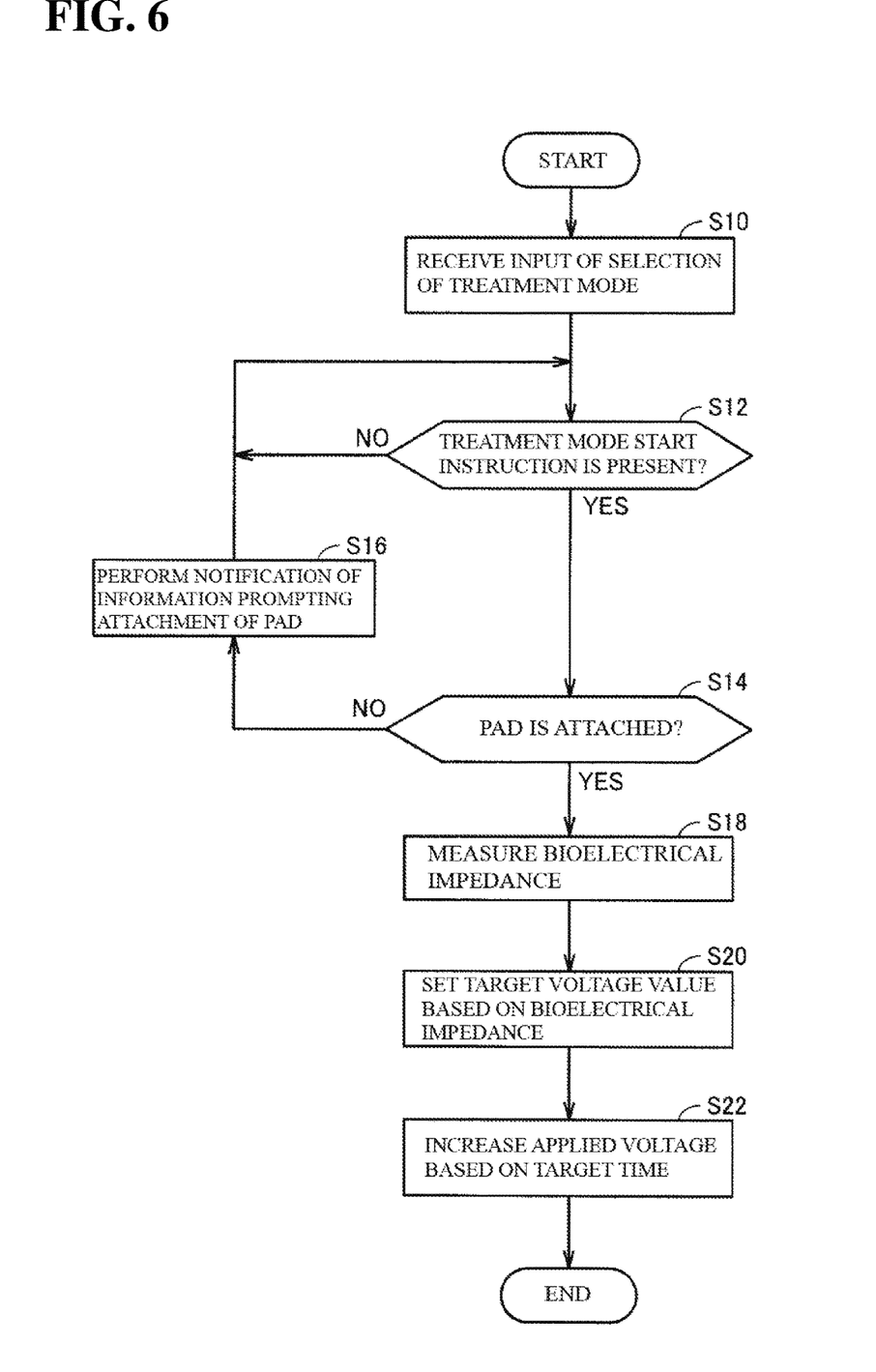
FIG. 6 is a flowchart showing an example of a processing procedure of an electric treatment device according to Preferred Embodiment 1 of the present invention.

FIG. 6 is a flowchart showing an example of a processing procedure of the electric treatment device 200 according to Preferred Embodiment 1. Typically, the steps shown in FIG. 6 are executed by the processor 210 of the electric treatment device 200.

With reference to FIG. 6, the electric treatment device 200 receives input of a selection of a treatment mode via the operation interface 230 (step S10). The electric treatment device 200 judges whether or not a treatment start instruction was received via the operation interface 230 (step S12). If no instruction has been received (NO in step S12), the electric treatment device 200 repeats the processing of step S12. If an instruction has been received (YES in step S12), the electric treatment device 200 judges whether or not the pair of pads 270 have been attached correctly by applying a minute voltage to the pair of pads 270 (step S14).

If the pair of pads 270 have not been correctly attached (NO in step S14), the electric treatment device 200 displays, on the display 260, information prompting the user to attach the pair of pads 270 to the treatment site (step S16), and the electric treatment device 200 executes the processing of step S12. If the pair of pads 270 have been correctly attached (YES in step S14), the electric treatment device 200 measures the bioelectrical impedance by applying a minute current to the treatment site via the pair of pads 270 (step S18).

The electric treatment device 200 sets the target time until the voltage applied between the pair of pads 270 reaches the target voltage value, based on the measured bioelectrical impedance and the target voltage value corresponding to the desirable stimulation intensity for the treatment mode selected in step S10 (step S20). The electric treatment device 200 increases the voltage value of the applied voltage based on the set target time (step S22). Then, the processing ends.

According to Preferred Embodiment 1, the user is able to receive comfortable electric stimulation suitable for the state of the body of the user, without performing a troublesome task.

Preferred Embodiment 2

In Preferred Embodiment 1, a configuration for performing treatment of a user with a single electric treatment device was described. In Preferred Embodiment 2, a configuration will be described in which a terminal apparatus and an electric treatment device are wirelessly connected and the electric treatment device performs treatment according to an instruction from the terminal apparatus. It should be noted that the terminal apparatus mainly carries out the roles of the operation interface 230 and the display 260 of the electric treatment device 200 in Preferred Embodiment 1.

Figure 7:
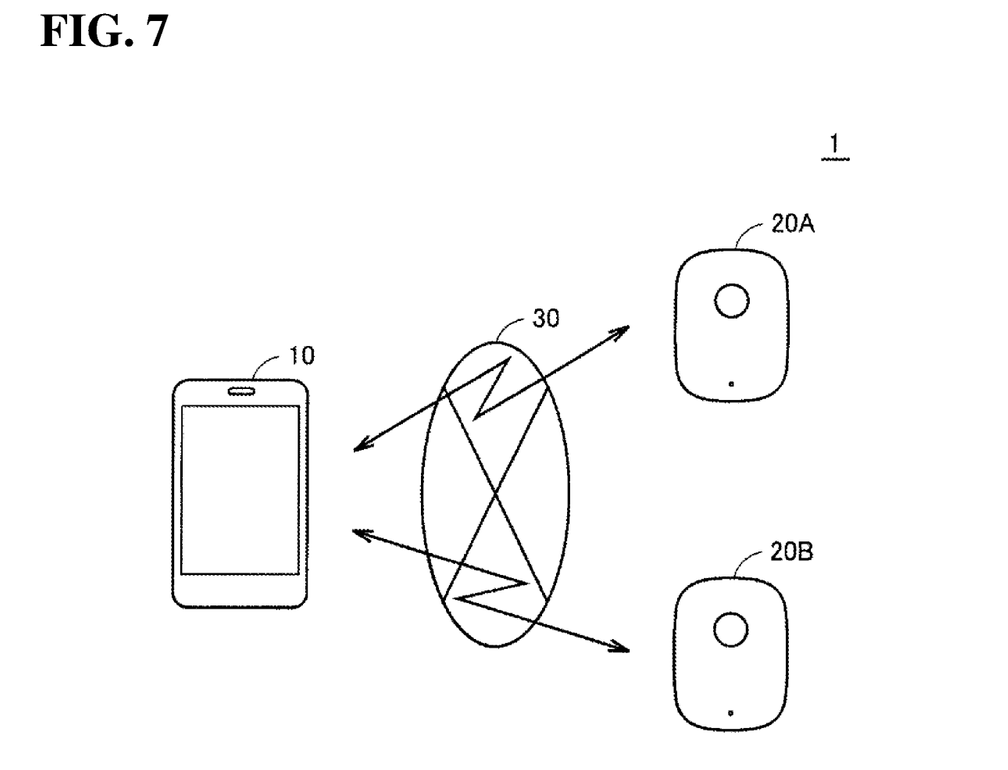
FIG. 7 is a diagram showing a schematic configuration of a treatment system according to Preferred Embodiment 2 of the present invention.

FIG. 7 is a diagram showing a schematic configuration of a treatment system 1 according to Preferred Embodiment 2. With reference to FIG. 7, the treatment system 1 includes a terminal apparatus 10, which is a user apparatus, electric treatment devices 20A and 20B, and a network 30. In the description below, when configurations and functions that are the same in the electric treatment devices 20A and 20B are described, the collective name "electric treatment device 20" will be used.

The electric treatment device 20 is of a cordless type and includes a pad, a holder, and a main body, which are integrated at the time of use, and these elements are combined to perform treatment. FIG. 7 shows only the main body of the electric treatment device 20 and the pad and holder are not illustrated. A specific configuration of the electric treatment device 20 will be described later.

The terminal apparatus 10 is a smartphone that includes a touch panel, for example. Hereinafter, description will be given taking a smartphone as a representative example of a "terminal apparatus". However, the terminal apparatus may also be another terminal apparatus such as a foldable mobile phone, a tablet terminal apparatus, a PC (personal computer), or a PDA (personal data assistant).

The network 30 to connect the terminal apparatus 10 and the electric treatment device 20 preferably uses a near-field wireless communication method, and typically BLE (Bluetooth (registered trademark) low energy) is used. For this reason, the terminal apparatus 10 and the electric treatment device 20 are BLE devices that have a function of performing wireless communication using BLE. However, the network 30 is not limited thereto, and another wireless communication method, such as Bluetooth (registered trademark) or wireless LAN (local area network) may also be employed.

In the treatment system 1 according to the present preferred embodiment, the terminal apparatus 10 uses an installed application to perform various types of instructions to the electric treatment devices 20A and 20B that have been connected through pairing. Also, the terminal apparatus 10 performs notification of necessary information to the user by displaying various types of information on the display 158. For example, the terminal apparatus 10 may also display information received from the electric treatment device 20 on the display 158.

Figure 8:
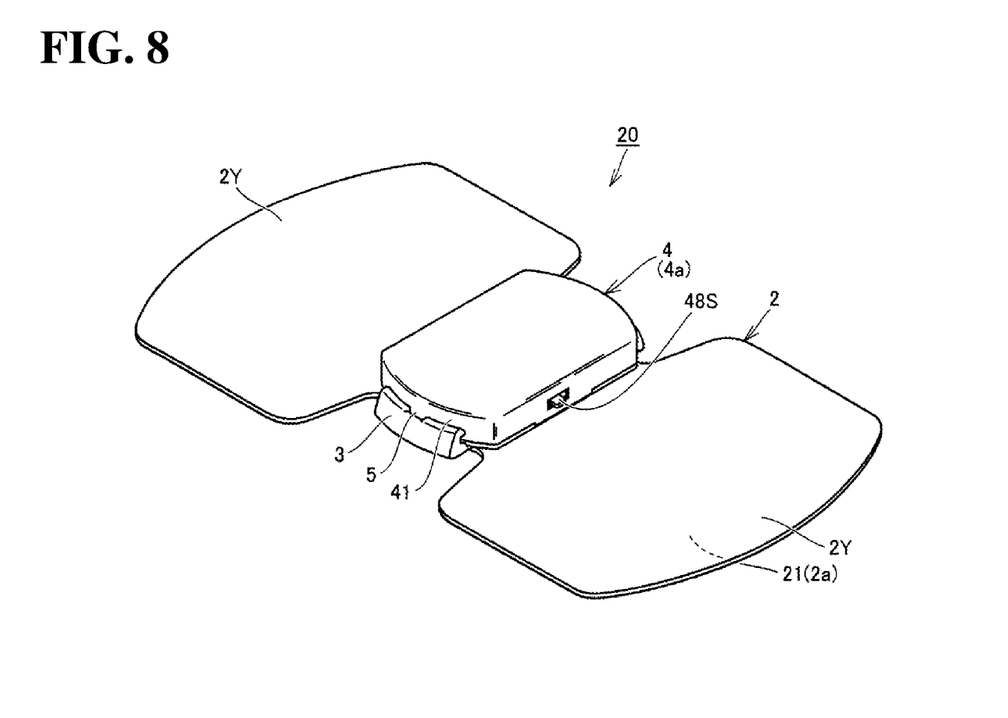
FIG. 8 is a perspective view showing a configuration of an electric treatment device according to Preferred Embodiment 2 of the present invention.
Figure 9:
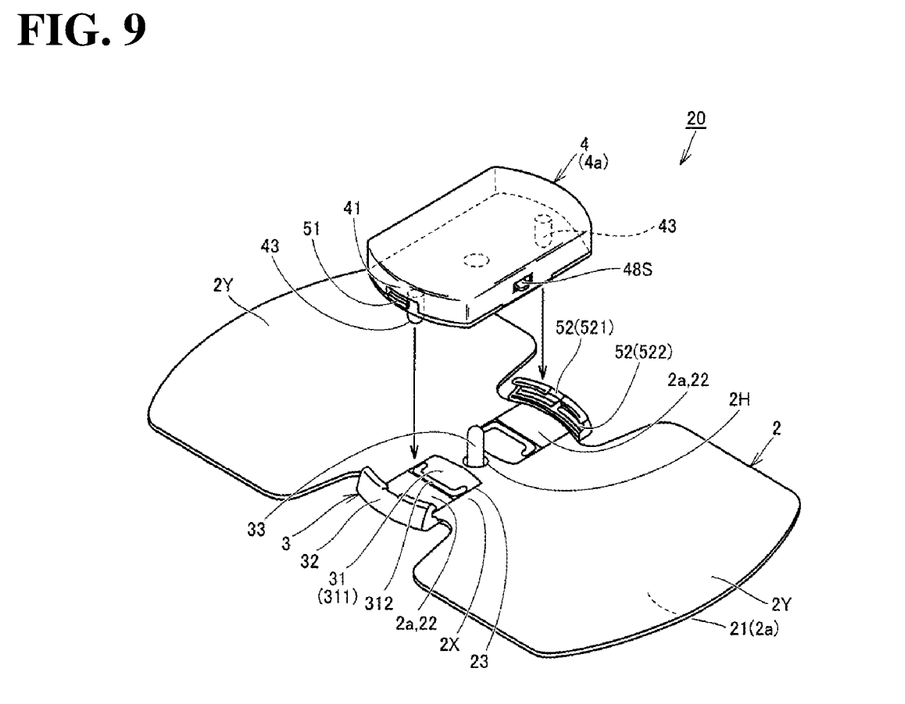
FIG. 9 is a perspective view showing a state in which a main body included in an electric treatment device according to Preferred Embodiment 2 of the present invention is separated from a holder and a pad 2.

FIG. 8 is a perspective view showing a configuration of the electric treatment device 20 according to Preferred Embodiment 2. FIG. 9 is a perspective view showing a state in which the main body 4 included in the electric treatment device 20 according to Preferred Embodiment 2 is separate from the holder 3 and the pad 2.

With reference to FIGS. 8 and 9, the electric treatment device 20 is a so-called cordless-type low-frequency treatment device, and includes the pad 2, the holder 3, and the main body 4.

The pad 2 is sheet-shaped and is attached to the body of the user. A conductive layer 2a is provided on a surface (lower surface) of a body-side portion 21 that faces the body on the outer surface of the pad 2. The pad 2 is adhered to the skin of the user using a conductive gel or the like, and a low-frequency pulse current is supplied to the user through the conductive layer 2a.

With reference to FIG. 9, the pad 2 has an attachment portion 2X and a treatment portion 2Y. The attachment portion 2X is held by the holder 3. The attachment portion 2X is provided with a window portion 23 and a through hole 2H. A positioning protrusion 312 of the holder 3 is arranged inside of the window portion 23. An interlock pin 33 of the holder 3 is inserted into the through hole 2H. The treatment portion 2Y is provided on both the left and right outer sides of the attachment portion 2X, and the conductive layer 2a is exposed at the body-side portion 21 of the treatment portion 2Y.

The conductive layer 2a is also exposed on the surface of the attachment portion 2X facing the main body 4, and this exposed portion defines a pad-side electrode portion 22. The pad-side electrode portion 22 is provided to electrically connect with the main body side electrode portion 43, a conductive layer 2a corresponding to one electrode portion (e.g., a cathode) is exposed at one end of the attachment portion 2X, and a conductive layer 2a corresponding to another electrode portion (e.g., an anode) is exposed at another end of the attachment portion 2X.

With reference to FIG. 9, the holder 3 includes a pad holding portion 31 that has a plate shape, and a pair of wall portions 32 that stand upright from both ends of the pad holding portion 31. The attachment portion 2X of the pad 2 is arranged on the upper surface 311 of the pad holding portion 31. Double-sided adhesive tape, paste, adhesive, or the like is arranged as needed between the upper surface 311 and the attachment portion 2X.

The pad holding portion 31 is provided with a positioning protrusion 312. The pad 2 is positioned with respect to the holder 3 by aligning the inner edge of the window portion 23 provided in the pad 2 with the positioning protrusion 312. An interlock pin 33 is also provided in the center of the pad holding portion 31. When the pad 2 is attached to the holder 3, the interlock pin 33 is inserted into the through hole 2H.

Since the pad 2 is a consumable item, during exchange, the pad 2 can be attached to and detached from the main body 4. In the present preferred embodiment, both the holder 3 and the pad 2 are integral due to the holder 3 holding the pad 2, and the main body 4 is configured to be attached to and detached from the pad 2 and the holder 3. The pad 2 is exchanged along with the holder 3, but it is not impossible to re-use the holder 3 as needed.

With reference to FIGS. 8 and 9, the main body 4 includes a case 4a having an approximately cuboid shape as an outer cover. A guiding engagement portion 5 (FIG. 8) is located between the case 4a and the holder 3 and the main body 4 (case 4a) is detachably attached to the holder 3. The guiding engagement portion 5 preferably includes a protrusion 51 (FIG. 9) located on the side surface 41 of the case 4a and a groove portion 52 (FIG. 9) located on the wall portion 32 of the holder 3.

With reference to FIG. 9, the groove portion 52 includes a vertical groove portion 521 and a horizontal groove portion 522. The vertical groove portion 521 is located in the vertical direction and is open upward. The horizontal groove portion 522 is provided in the horizontal direction and the two ends are open. When the main body 4 is to be attached to the holder 3, the protrusion 51 and the groove portion 52 are both moved close to each other in opposing directions and are engaged. The engagement between the holder 3 and the main body 4 is canceled by rotating the main body 4 with respect to the holder 3, and the main body 4 is able to be removed from the holder 3.

When the main body 4 is attached to the holder 3, a low-frequency pulse current is supplied to the conductive layer 2a of the pad 2. Specifically, the main body includes: a pair of main body-side electrodes 43; a substrate (not shown); an electrical circuit (not shown); and an interlock mechanism (not shown). The electrical circuit includes various types of control devices and is mounted on the surface of a substrate.

The control devices include a processor configured or programmed to execute various processes, a memory to store programs, data, and the like, a communication interface to wirelessly communicate various types of data with the terminal apparatus 10, a waveform generation/output apparatus to boost the power source voltage, and perform generation, output, and the like of the low-frequency pulse current (treatment current), and the like.

The substrate, electrical circuit, and interlock mechanism are provided inside of the main body 4 (case 4a). A power source (not shown) such as a battery is provided inside of the main body 4 (case 4a). A switch 48S (FIG. 2), a display (not shown) such as an LED (light emitting diode), a button (not shown), and the like are provided outside of the case 4a.

In the state in which the main body 4 is attached to the holder 3, the leading end portion of the main body-side electrode portion 43 comes into contact with the pad-side electrode portion 22. Accordingly, the main body-side electrode portion 43 and the pad-side electrode portion 22 are electrically connected and the electrical circuit can supply the low-frequency pulse current to the pad-side electrode portion 22.

Figure 10:
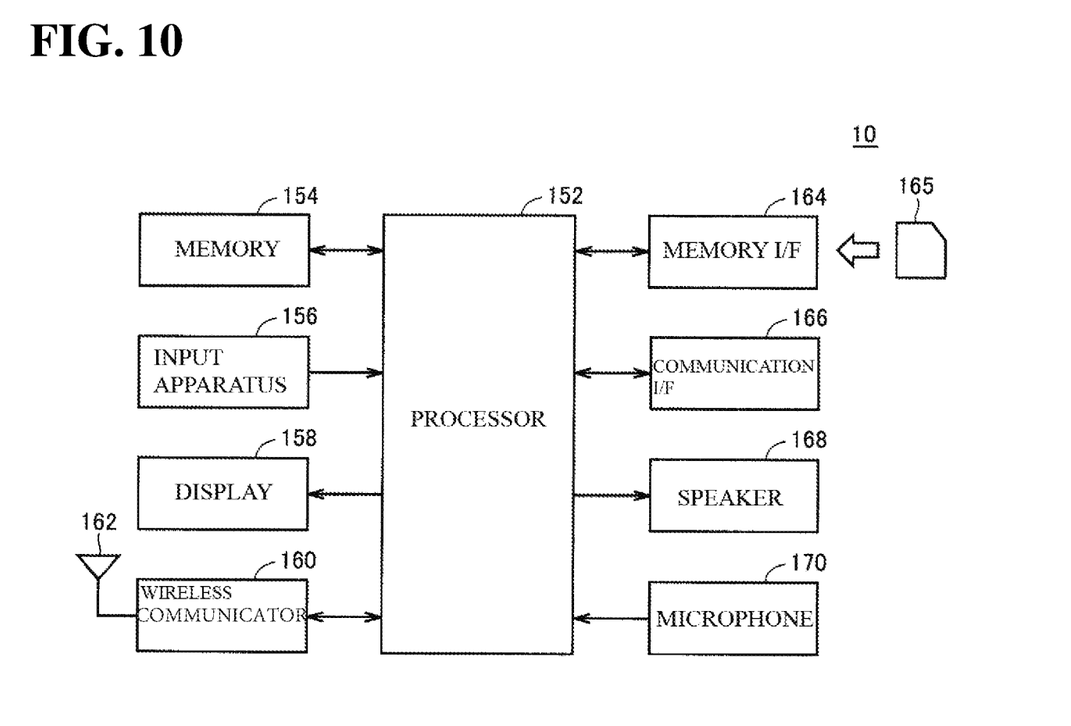
FIG. 10 is a block diagram showing an example of a hardware configuration of a terminal apparatus according to Preferred Embodiment 2 of the present invention.

FIG. 10 is a block diagram showing an example of a hardware configuration of the terminal apparatus 10 according to Preferred Embodiment 2. With reference to FIG. 10, the terminal apparatus 10 includes a processor 152, a memory 154, an input interface 156, a display 158; a wireless communicator 160, a memory interface (I/F) 164, a communication interface (I/F) 166; a speaker 168, and a microphone 170.

The processor 152 is typically an arithmetic processing unit such as a CPU (central processing unit) or an MPU (multi-processing unit). The memory 154 is realized by a RAM (random access memory), a ROM (read-only memory), a flash memory, or the like.

The input interface 156 receives input of an operation to the terminal apparatus 10. Typically, the input interface 156 is realized by a touch panel. The touch panel is provided on the display 158, and, for example, the touch panel is of an electrostatic capacitive type. The touch panel detects a touch operation on the touch panel performed by an external object each predetermined amount of time, and inputs the touch coordinates to the processor 152. However, the input interface 156 may also include buttons or the like.

The wireless communicator 160 is connected to a mobile communication network via a communication antenna 162 and transmits and receives signals for wireless communication. Accordingly, the terminal apparatus 10 is able to communicate with another communication apparatus via the mobile communication network, such as LTE (long term evolution), for example.

The memory interface 164 reads out data from an external storage medium 165. The processor 152 reads out the data stored in the storage medium 165 via the memory interface 164 and stores the data in the memory 154. The processor 152 reads out the data from the memory 154 and stores the data in the external storage medium 165 via the memory interface 164.

The storage medium 165 includes a medium that stores a program in a non-volatile manner, such as a CD (compact disc), a DVD (digital versatile disk), a BD (Blu-ray (registered trademark) Disc), a USB (universal serial bus) memory, or an SD (secure digital) memory card.

The communication interface (I/F) 166 exchanges various types of data between the terminal apparatus 10 and the electric treatment device 20, and is realized by an adapter, a connector, and the like. A wireless communication method achieved through, for example, BLE (Bluetooth (registered trademark) low energy), a wireless LAN, or the like is used as the communication method.

The speaker 168 converts an audio signal provided from the processor 152 into audio and outputs the audio to the outside of the terminal apparatus 10. The microphone 170 receives audio input to the terminal apparatus 10 and provides an audio signal corresponding to the audio input to the processor 152.

The electric treatment device 20 has the same function as the above-described electric treatment device 200.

Specifically, the same function as the electric treatment device 200 shown in FIG. 5 is achieved by a controller included in the main body 4 of the electric treatment device 20. In Preferred Embodiment 1, the user provided various types of information to the electric treatment device 200 via the operation interface 230. In Preferred Embodiment 2, the user provides various instructions to the terminal apparatus 10 via the input interface 156 and indirectly provides the various instructions to the electric treatment device 20 due to the instructions being transmitted from the terminal apparatus 10 to the electric treatment device 20.

Also, in Preferred Embodiment 1, a configuration was used in which the treatment current is applied to the treatment site by applying a voltage between the electrode of one pad 270 with a positive polarity and the electrode of another pad 270 with a negative polarity. In Preferred Embodiment 2, a configuration is used in which two electrode portions corresponding to a positive polarity and a negative polarity are provided on one pad 2, and the treatment current is applied to the treatment site due to a voltage being applied between the electrodes.

Also, the various types of information stored in the memory 220 in order for the electric treatment device 200 to execute the above-described processing in Preferred Embodiment 1 are typically stored in the memory of the electric treatment device 20. However, a configuration may also be used in which some of the information (e.g., the desirable stimulation intensity, or the like) is stored in the memory 154 of the terminal apparatus 10.

It should be noted that a configuration may also be used in which the electric treatment device 20 transmits information that is necessary for warning the user, information to be stored in the terminal apparatus 10, and the like to the terminal apparatus 10.

In FIGS. 3 and 4 described above, a configuration in which the voltage value is increased in proportion with time was described, but there is no limitation to this configuration, and it is also possible to use a configuration in which the voltage value is increased in a curvilinear manner.

In the above-described Preferred Embodiment 1, a configuration in which a pair of pads 270 is used was described, but there is no limitation to this configuration, and it is also possible to use a configuration in which an electrode for a positive polarity and an electrode for a negative polarity are provided on one pad.

In the above-described preferred embodiment, a program for causing a computer to function to execute controls such as those described in the above-described flowchart can also be provided. This kind of program can also be recorded on a non-transitory computer-readable recording medium such as a flexible disk belonging to a computer, a CD-ROM (compact disk read only memory), a secondary storage apparatus, a main storage apparatus, and a memory card, and can be provided as a program product. Alternatively, a program can also be provided by being recorded on a recording medium such as a hard disk built into a computer. A program can also be provided through downloading via a network.

The program may cause a computer to execute processing by calling a needed module in a predetermined sequence and at a predetermined timing from among program modules provided as part of the operating system (OS) of the computer. In this case, the above-described module is not included in the program itself, and processing is executed in cooperation with the OS. This program that does not include the module can also be included in the program according to the present preferred embodiment.

The program according to the present preferred embodiment may also be provided incorporated with part of another program. In this case as well, the module included in the other program is not included in the program itself, and processing is executed in cooperation with the other program. This program incorporated in the other program can also be included in the program according to the present preferred embodiment.

The configurations described as the above-described preferred embodiments are examples of configurations of the present invention and can also be combined with another known technique, and it is also possible to perform modifications, such as omitting a portion, without departing from the gist of the present invention. Also, a case is also possible in which the above-described preferred embodiments are carried out by employing processing and configurations described in another preferred embodiment as appropriate.

The preferred embodiments disclosed herein are to be considered exemplary and non-limiting in all respects. The scope of the present invention is indicated not by the above description, but by the claims, and meanings equivalent to the claims and all modifications within the scope are intended to be encompassed therein.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. An electric treatment device comprising:
    an impedance detector to measure bioelectrical impedance at a site of a body of a user, using a plurality of electrodes in contact with the site;
    a voltage controller to perform treatment of the site by controlling an applied voltage that is applied to the plurality of electrodes; and
    a timer to set a target time from when treatment of the site is started by the voltage controller to when a voltage value of the applied voltage reaches a target voltage value, based on the measured bioelectrical impedance; wherein
    the timer sets the target time to be shorter the greater the measured bioelectrical impedance is; and
    the voltage controller increases the voltage value of the applied voltage to the target voltage value based on the set target time.

2. The electric treatment device according to claim 1, wherein the voltage controller increases the voltage value of the applied voltage such that a second increase rate of the voltage value in a period from a time when the voltage value of the applied voltage reaches a predetermined reference value to when the target voltage value is reached is smaller than a first increase rate of the voltage value in a period from when treatment of the site is started to when the voltage value of the applied voltage reaches the predetermined reference value.

3. The electric treatment device according to claim 1, wherein
    the electric treatment device includes a plurality of treatment modes;

the target voltage value is determined in advance for each of the plurality of treatment modes; and the timer sets the target time based on the measured bioelectrical impedance and the target voltage value corresponding to a treatment mode selected by the user from the plurality of treatment modes.

4. The electric treatment device according to claim 1, wherein the target voltage value is a voltage value corresponding to an intensity of electric stimulation desired by the user.

5. The electric treatment device according to claim 1, wherein the electric treatment device is a low-frequency treatment device.

6. A treatment system comprising:

a terminal apparatus; and an electric treatment device able to perform wireless communication with the terminal apparatus; wherein the electric treatment device includes:

an impedance detector to measure bioelectrical impedance at a site of a body of a user, using a plurality of electrodes in contact with the site;

a voltage controller to perform treatment of the site by controlling an applied voltage that is applied to the plurality of electrodes; and a timer to set a target time from when treatment of the site is started by the voltage controller to when a voltage value of the applied voltage reaches a target voltage value, based on the measured bioelectrical impedance; wherein the timer sets the target time to be shorter the greater the measured bioelectrical impedance is; and the voltage controller increases the voltage value of the applied voltage to the target voltage value based on the set target time.

* * * * *